(12) United States Patent
Strong

(10) Patent No.: US 8,613,955 B2
(45) Date of Patent: Dec. 24, 2013

(54) METHODS OF PRODUCING MICROPARTICLES

(75) Inventor: Peter Strong, Oxon (GB)

(73) Assignee: Mucovax Inc., Nassau (BS)

( * ) Notice: Subject to any disclaimer, the term of this patent is extended or adjusted under 35 U.S.C. 154(b) by 341 days.

(21) Appl. No.: 12/432,875

(22) Filed: Apr. 30, 2009

(65) Prior Publication Data
US 2009/0270347 A1 Oct. 29, 2009

Related U.S. Application Data

(63) Continuation-in-part of application No. PCT/GB2007/004129, filed on Oct. 29, 2007.

(60) Provisional application No. 60/855,185, filed on Oct. 30, 2006.

(51) Int. Cl.
*A61K 9/16* (2006.01)

(52) U.S. Cl.
USPC .................... 424/493; 514/54; 536/123.1

(58) Field of Classification Search
USPC .................... 424/493; 514/54; 536/123.1
See application file for complete search history.

(56) References Cited

U.S. PATENT DOCUMENTS

| 5,218,020 A | 6/1993 | Tung et al. |
| 2002/0071870 A1 | 6/2002 | Sharma |

FOREIGN PATENT DOCUMENTS

| CA | 2375992 | * | 1/2001 | ............... A61K 9/14 |
| DE | 199 32 157 | | 1/2001 | |
| JP | 63-170991 | * | 7/1988 | ............. C08B 37/08 |
| WO | WO 03/015744 | | 2/2003 | |

OTHER PUBLICATIONS

English abstract of foreign patent JP63-179901, retrived on May 16, 2011 from database of Chemical Abstract Services—STN, 1 page.*
Vrtala et al, Methods, 2004, 32, 313-320.*
Gennaro, A. R., Remington: The Science and Practice of Pharmacy, 19th edition, 1995, Mack Publishing Company, 2 pages.*
Y. Shibata et al., "Oral Administration of Chitin Down-Regulates Serum IgE Levels and Lung Eosinophilia in the Allergic Mouse" Journal of Immunology, The Williams and Wilkins Co. Baltimore, vol. 164, No. 3, Jan. 1, 2000, pp. 1314-1321, XP001113079 ISSN: 0022-1767.

* cited by examiner

*Primary Examiner* — Elli Peselev
(74) *Attorney, Agent, or Firm* — Vedder Price P.C.; Thomas J. Kowalski; Deborah L. Lu

(57) ABSTRACT

Methods of producing microparticles, and especially chitin microparticles (CMP), are disclosed that involve reducing the size of (larger) particles using a (high shear) microfluidising instrument.

10 Claims, 9 Drawing Sheets

| Size class [μm] | p3 [%] | Q3 [%] | Size class [μm] | p3 [%] | Q3 [%] |
|---|---|---|---|---|---|
| 0.7 - 0.9 | 0.3 | 1.2 | 11.8 - 14.3 | 4.4 | 27.7 |
| 0.9 - 1.0 | 0.4 | 1.6 | 14.3 - 17.3 | 5.7 | 33.4 |
| 1.0 - 1.2 | 0.4 | 2.0 | 17.3 - 20.8 | 6.2 | 39.6 |
| 1.2 - 1.5 | 0.6 | 2.6 | 20.8 - 25.2 | 6.4 | 46.0 |
| 1.5 - 1.8 | 0.7 | 3.3 | 25.2 - 30.4 | 7.4 | 53.3 |
| 1.8 - 2.2 | 0.9 | 4.2 | 30.4 - 36.7 | 8.7 | 62.0 |
| 2.2 - 2.6 | 1.2 | 5.4 | 36.7 - 44.3 | 9.4 | 71.4 |
| 2.6 - 3.2 | 1.5 | 6.9 | 44.3 - 53.5 | 9.1 | 80.6 |
| 3.2 - 3.8 | 1.9 | 8.8 | 53.5 - 64.5 | 8.0 | 88.6 |
| 3.8 - 4.6 | 2.2 | 11.0 | 64.5 - 77.9 | 5.8 | 94.5 |
| 4.6 - 5.6 | 2.3 | 13.3 | 77.9 - 94.1 | 2.9 | 97.3 |
| 5.6 - 6.7 | 2.2 | 15.5 | 94.1 - 113.6 | 1.5 | 98.8 |
| 6.7 - 8.1 | 2.2 | 17.7 | 113.6 - 137.2 | 0.8 | 99.6 |
| 8.1 - 9.8 | 2.5 | 20.2 | 137.2 - 165.6 | 0.3 | 99.9 |
| 9.8 - 11.8 | 3.1 | 23.3 | 165.6 - 200.0 | 0.1 | 100.0 |
| | | | 200.0   1250.0 | 0.0 | 100.0 |

| Characteristics | |
|---|---|
| Q3 [%] | x[μm] |
| 10.0 | 4.3 |
| 50.0 | 28.0 |
| 90.0 | 66.9 |

METHODS OF PRODUCING MICROPARTICLES

INCORPORATION BY REFERENCE

This application is a continuation-in-part application of international patent application Serial No. PCT/GB2007/004129 filed Oct. 29, 2007, which published as PCT Publication No. WO 2008/053192 on May 8, 2008, which claims benefit of U.S. provisional patent application Ser. No. 60/855,185 filed Oct. 30, 2006.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to methods of producing microparticles, in particular chitin microparticles (CMP).

The invention also relates to methods of formulating the microparticles in pharmaceutical compositions and methods of making kits comprising the microparticles.

BACKGROUND OF THE INVENTION

Studies by Shibata et al (1-4) have shown that oral delivery of 1-10 µm phagocytosable chitin particles results in an elevation of Th1 cytokines in mouse spleen cell cultures. The effect was specific to the particulates as no elevation was produced by soluble chitin. It could also be reproduced in 1 µm polystyrene microspheres coated with N-Acetyl-D-Glucosamine, which is the main component of chitin. It was also demonstrated that oral administration of chitin down-regulates serum IgE and lung eosinophilia in a murine model of ragweed allergy (1).

Shibata et al have also developed a mouse model of allergic airway inflammation and orally administered chitin preparations to the mice (Shibata 2000). Ragweed-specific IgE levels were significantly reduced after daily oral administration of chitin to ragweed-sensitised mice, before and during immunisation.

When chitin was administered prophylactically to mice who were subsequently administered ragweed, IL-4, IL-5 and IL-10 production was significantly reduced and low but significant levels of IFN-γ were detected.

Chitin also has a prophylactic effect when administered to C57BL6 mice, which are higher responders for cell-mediated immunity/Th1 responses, but lower responders for allergic responses compared with BALB/c mice. When ragweed-sensitised mice were treated simultaneously with ragweed and chitin, the levels of IL-4, IL-5 and IL-10 produced were significantly reduced compared to those stimulated by ragweed alone.

In Applicants' earlier application, WO 03/015744, Applicants described experiments in mice which demonstrated that a suspension of CMP in saline administered intranasally has beneficial immune modulating properties, which can be applied for the treatment of allergic disease and can enhance protection by up-regulation of mechanisms of innate immunity against viral and bacterial infections of the respiratory tract. The beneficial immune regulating properties can also be applied for the treatment of conditions that would benefit from an up-regulation of natural killer (NK) cell activity and/or the secretion of interferon-γ (IFN-γ), such as the treatment of cancer.

In Applicants' earlier application, U.S. 60/815,074, Applicants described the use of CMP as an adjuvant in vaccine compositions. In particular, CMP compositions were found to be capable of synergistically enhancing the protection raised against an antigen from an infectious agent when the CMP compositions were combined with a further adjuvant, such as the cholera toxin B subunit (CTB).

The evidence to date supports the concept that for CMP to be optimally effective the particles should be micronized and fall in the range of 1 to 20 µm. The primary mode of action of CMP depends on phagocytosis by macrophages and other phagocytes and consequently the CMP need to be of a phagocytosable size, which is generally considered to be in the range of 1 to 20 µm.

Chitin is manufactured from shrimp shell waste, which is a by-product of the shrimp processing industry. The shells are treated with acid and alkali to remove minerals and protein contaminants. The purified chitin flakes are then milled by standard milling methods to produce a powder with a particle size approximately between 100 to 200 µm. This is the starting material for the production of CMP.

In the methods described by Shibata and Strong (3, 5) chitin powder was micronized by sonication in the laboratory. However, this method has the disadvantage of not being amenable for scale-up to industrial manufacturing needs and there are no suitable Good Manufacturing Practice (GMP) protocols established for the micronization of insoluble polysaccharides such as chitin. There is also the further problem that the usual use of sonication is for disruption of agglomerates and cell shearing and sonication does not produce uniform sized particles of CMP.

Citation or identification of any document in this application is not an admission that such document is available as prior art to the present invention.

SUMMARY OF THE INVENTION

In view of the above drawbacks Applicants have investigated other methods that are capable of reducing particle size, such as air-jet milling and dry powder ball milling, that would be more suitable for industrial scale-up. Air-jet milling is the method of choice in the pharmaceutical industry for producing uniform powders of drugs for formulation into tablets. However, when Applicants investigated air-jet milling as a method for the production of CMP Applicants found that after three passes the average particle size was still greater than 100 µm, indicating that this method is completely ineffective for producing CMP. Applicants also found that dry powder ball milling is an unsatisfactory method for producing CMP because the time required to produce particles approaching a phagocytable size was excessive, i.e. of the order of days, and even then the average particle size was around 50 µm rather than the more desirable 10 µm. In addition, the excessive milling time is likely to produce metal contamination from wear to the metal balls.

Microfluidising instruments (microfluidisers), have previously been used in the manufacture of paints and inks. However, Applicants have now surprisingly found that microfluidising instruments may also be used to produce CMP of a phagocytosable size, and thus CMP produced using a microfluidising instrument are appropriate for use as a pharmaceutical and for formulation in pharmaceutical compositions. In particular, Applicants have found that advantages of using a microfluidising instrument to produce CMP include the ability to handle large volumes and the ease of scale up for industrial manufacturing needs; GMP protocols have been developed; it produces a homogenous product with greater control over particle size than other methods; and it gives a greater yield of CMP than other methods.

Thus, the present invention broadly relates to methods of producing microparticles, for example CMP, by reducing the size of (larger) particles using a (high shear) microfluidising instrument.

Essentially, microfluidising instruments suitable for use in the invention reduce particle size by propelling a product (e.g. a suspension) through geometrically fixed micro channels at high pressure, e.g. 20,000 to 30,000 psi, and high velocity, e.g. in excess of 500 ms$^{-1}$. This provides an extremely focused interaction zone. As the product passes through the microchannels, forces produced by the high pressure act upon the product to reduce the size of particles in the product, including shear forces, through deformation of the product stream occurring from contact with the walls of the microchannels; impact forces, through collisions occurring when the high velocity product stream impinges upon itself; and cavitation forces, through formation and collapse of vapour cavities within the product stream.

Examples of microfluidising instruments suitable for use in the invention include the Microjet Laboratory Processor Model 100 from Microjet Technology and Microfluidizer® Processors from Microfluidics™.

Applicants have also realised that the advantages of using microfluidising instruments to produce CMP are also applicable to the production of any other insoluble polysaccharide microparticles. In particular, microfluidising instruments may be advantageously used to produce insoluble polysaccharide particles that are of phagocytosable size and/or are useful in methods of medical treatment and/or which may be provided in pharmaceutical compositions.

For example, chitosan is a deacylated derivative of chitin and is an insoluble polysaccharide. Danbiosyst have filed patent applications in which chitosan is used as a drug delivery system, in particular for targeting the mucosa of patients, see for example U.S. Pat. No. 5,690,954 which describes a drug delivery system in which chitosan microspheres may be 10 to 100 µm.

Accordingly, in a first aspect of the invention there is provided a method of producing a collection of microparticles by reducing the size of particles, comprising:
  (a) making a suspension of a collection of particles;
  (b) passing the suspension through a microfluidising instrument to reduce the average diameter of the particles in the collection of particles to the desired average diameter;
  wherein the particles are insoluble polysaccharide particles.

Preferably the microfluidising instrument (microfluidiser) is a high shear microfluidising instrument (high shear microfluidiser), such as a high pressure microfluidising instrument (high pressure microfluidiser) or high shear particle disintegration device. For example, the microfluidising instrument is preferably capable of operating at a pressure of at least 10,000 psi, more preferably at least 15,000 psi, even more preferably at least 20,000. In particular, the microfluidising instrument is preferably capable of operating in the range of 10,000 to 30,000 psi, more preferably 15,000 to 30,000 psi, even more preferably 20,000 to 30,000 psi, and most preferably 20,000 to 23,000 psi.

The method is preferably for producing a collection of chitin and/or chitosan microparticles, e.g. a chitin microparticle or chitosan microparticle preparation, in which case the particles to be reduced in size are chitin and/or chitosan particles. If desired, the collection of particles of step (a) may include a mixture of chitin and chitosan particles. More preferably the method is for producing CMP, in which case the particles to be reduced in size are chitin particles.

Chitin is a polymer of N-acetyl-D-glucosamine and has a similar structure to cellulose. It is an abundant polysaccharide in nature, comprising the horny substance in the exoskeletons of crab, shrimp, lobster, cuttlefish, or insects. It is also found in fungi.

It will be recognised by those skilled in the art that as chitin is derived from a natural material, there is a variation in its composition and there may be low levels of deacetylated units that naturally occur in the chitin polymer. However, it is preferred that when the method is for producing CMP, the deactylated units in the collection of chitin particles comprise less than 20% of the total units, more preferably less than 15% of the total units, even more preferably less than 10% of the total units and most preferably less than 5% of the total units.

Additionally, the method may be for producing synthetic CMP, in which case, the insoluble polysaccharide particles to be reduced in size are synthetic chitin particles. Synthetic chitin particles may be carrier particles e.g. formed form a biocompatible material such as polystyrene or latex, coated with N-acetyl-D-glucosamine, chitin or chitin fragments. Alternatively, synthetic chitin may be synthesised by chemical or enzymatic techniques. For example, chitin particles may be produced by polymerisation of actylglucosamine, for example N-acetyl-D-glucosamine.

As the pharmaceutical effects caused by CMP have been found to be size dependent, it is preferable that the microparticles produced by the method have a diameter such that they are capable of producing a pharmaceutical effect. Thus it is preferable that the collection of microparticles produced by the method includes microparticles having a diameter of phagocytosable size, e.g. within the range of 1 to 20 µm. For example, the desired average diameter of the microparticles in the collection of microparticles may be 50 µm or less, 40 µm or less, 30 µm or less, 20 µm or less, 15 µm or less, 10 µm or less, or even 5 µm or less. Preferably the desired average diameter is a phagocytosable size, e.g. within the range of 1 to 20 µm, 1 to 15 µm, or 1 to 10 µm. For example, the desired average diameter may be within the range of 5 to 15 µm, 6 to 14 µm, 7 to 13 µm, 8 to 12 µm, 9 to 11 µm or even 9 to 10 µm. Preferably the microparticles are at least 1 µm in diameter. Preferably the standard deviation of the microparticles in the collection of microparticles is 10 µm or less, 8 µm or less, 5 µm or less, or 3 µm or less. Most preferably the average diameter of the microparticles in the collection of microparticles is within the range of 1 to 15 µm and the standard deviation of the particles in the collection is 5 µm or less.

The term "microparticle" refers to a particle having a diameter of 100 µm or less. Thus, a "collection of microparticles" refers to a collection of particles in which all or substantially all, e.g. at least 90%, preferably at least 95%, more preferably at least 99%, of the particles in the collection have a diameter of 100 µm or less. A "particle" may be a microparticle, and a "collection of particles" may include microparticles, and/or may consist substantially of, or entirely of, microparticles.

The term "average diameter" refers to the mean average diameter, and for the avoidance of doubt, the term "particle diameter" is interchangeable with the term "particle size", and vice versa.

It is believed that microparticles having a diameter within the range of 1 to 20 µm will be optimally pharmaceutically effective. Thus, the particle size distribution of the microparticles in the collection of microparticles is such that the diameter of at least 50%, 60%, 70%, 80%, 90%, 95%, or 99%, or substantially all of the microparticles is preferably less than 20 µm, and/or within the range of 1 to 20 µm. For example, the diameter of at least 50% of the microparticles in the collection of microparticles may be less than 20 µm, and/or within the range of 1 to 20 µm, 5 to 20 µm, 5 to 15 µm, 6 to 14 µm, 7 to 13 µm, 8 to 12 µm, 9 to 11 µm, or 9 to 10 µm. Preferably the diameter of at least 70% of the microparticles in the collection of microparticles is less than 20 µm, and/or within the range of 1 to 20 µm, 5 to 20 µm, 5 to 15 µm, 6 to 14 µm, 7 to 13 µm, 8 to 12 µm, 9 to 11 µm, or 9 to 10 µm. More preferably the diameter of at least 80% of the microparticles in the collection of microparticles is less than 20 µm, and/or within the range of 1 to 20 µm, 5 to 20 µm, 5 to 15 µm, 6 to 14 µm, 7 to 13 µm, 8 to 12 µm, 9 to 11 µm, or 9 to 10 µm. More preferably the diameter of at least 90% of the microparticles in the collection of microparticles is less than 20 µm, and/or within the range of 1 to 20 µm, 5 to 20 µm, 5 to 15 µm, 6 to 14 µm, 7 to 13 µm, 8 to 12 µm, 9 to 11 µm, or 9 to 10 µm.

For the avoidance of doubt the term "within the range of" includes the specified range limits. For example, a collection of particles having diameters within the range of 1 to 20 µm includes particles having diameters of 1 µm and 20 µm.

Particle size and particle size distribution may be determined by the method of Single-Particle Optical Sensing (SPOS), also known as Optical Particle Counting (OPC). This is well known in the art. Particle size is determined by passing particles one at a time between a laser beam and a detector. As a particle passes between the laser beam and the detector it causes a change in the amount of light from the laser beam incident on the detector. The size of the particle is determined by comparing the change in the amount of incident light caused by a particle of interest with the change in the amount of incident light caused by a reference particle, e.g. a substantially uniform particles of known size, e.g. of known diameter. This may involve reference to a calibration curve generated using such particles of known size.

Typically, the change in the amount of light incident on the detector caused by the passage of a particle between the laser beam and the detector generates an electronic signal. The size of the particle is then determined by comparing the magnitude of the signal generated by the particle of interest with the magnitude of the signals generated by reference particles, e.g. substantially uniform particles of known size, e.g. known diameter.

Thus, the term "particle diameter" refers to the diameter of a reference particle, e.g. a substantially uniform particle of known size, that generates the same signal as the particle of interest as measured by a method of Single-Particle Optical Sensing.

Thus, the particle size distribution, e.g. the percent value of particles, e.g. microparticles, in a collection having a diameter within a particular range, e.g. 1 to 20 µm, may be determined by measuring diameters of particles in the collection using a Single-Particle Optical Sensing method. This may involve measuring the diameters of the particles in a sample taken from a collection and extrapolating the data obtained, such that the particle size distribution in the sample is considered to be representative of the particle size distribution in the collection. Alternatively, the diameter of all or substantially all the particles in a collection may be measured to determine the particle size distribution of the collection.

Applicants have found that the diameter of microparticles produced using a microfluidising instrument is determined, at least in part, by the number of times the suspension of the collection of particles is passed through, i.e. iteratively passed through, the microfluidising instrument. Thus, the method preferably comprises passing the suspension through the microfluidising instrument a sufficient number of times to reduce the average diameter of the particles in the collection to the desired average diameter. Preferably the method comprises passing the suspension through the microfluidising instrument at least 7 times or more, more preferably at least 9 times or more.

Increasing the operating pressure of the microfluidising instrument, i.e. the pressure at which the suspension is passed through the microfluidising instrument, and/or adjusting the size e.g. diameter, and/or geometry of the microchannels may affect, e.g. reduce, the number of times the suspension must be passed through the microfluidising instrument to reduce the average diameter of the particles in the collection to the desired average diameter. Applicants have found that the use of an operating pressure and a size and geometry of microchannels such that the suspension is passed through the microfluidising instrument at least 7 times or more, more preferably at least 9 times or more, is optimal for minimising overheating and/or blockage of the microfluidising instrument. The person skilled in the art is able to select such an appropriate operating pressure and size and geometry of the microchannels.

The operating pressure is preferably at least 10,000 psi or more, more preferable at least 15,000 psi or more, even more preferably at least 20,000 psi or more. Preferably the operating pressure is within the range of 20,000 to 30,000 psi, more preferably within the range of 20,000 to 23,000 psi.

The method may also comprise sieving the collection of particles prior to passing the particles through the microfluidising instrument. A collection of particles may include particles that are large enough to block the microchannels, e.g. particles having a diameter of 50 µm or larger, and thus sieving the collection of particles prior to passing the particles though the microfluidising instrument would reduce the possibility of particles blocking the microchannels. Sieving also allows the starting size of the particles to be reduced. This can be advantageous, as Applicants have found that the yield of microparticles increases as the size of the starting particles decreases. Thus, preferably the method comprises sieving the collection of particles prior to making the suspension and/or passing the collection of particles through the microfluidising instrument. Preferably the sieve has a pore size of 200 µm or less, 150 µm or less, or 100 µm or less. Most preferably the sieve has a pore size of 126 µm.

Methods of sieving particles are well known in the art. The collection of particles may be sieved prior to making the suspension of step (a), for example by using an electronic shaker sieve, or after making the suspension of step (a) but prior to passing the suspension through a microfluidising instrument, for example by passing the suspension though a filter, e.g. filter paper.

Preferably the average diameter of the collection of particles prior to making the suspension of step (a) and/or prior to sieving the collection of particles is greater than 100 µm, more preferably within the range of 100 to 200 µm. Preferably the collection of particles prior to making the suspension of step (a) and/or prior to sieving the collection particles have diameters less than about 300 µm. Preferably the insoluble polysaccharide particles have been milled prior to making the suspension of step (a). Such milling may be performed using any suitable standard milling procedure. The term "chitin powder" refers to chitin raw material, e.g. the particles have an average diameter greater than 100 µm, preferably within the range of 100 to 200 µm, and preferably less than about 300 µm.

In an alternative aspect, the present invention provides a method of producing a collection of chitin and/or chitosan microparticles by reducing the size of chitin and/or chitosan particles, comprising:
(a) making a suspension of a collection of chitin and/or chitosan particles;
(b) passing the suspension through a microfluidising instrument, for example 9 times or more, to reduce the average diameter of the chitin and/or chitosan particles in the collection of particles to the desired average diameter, wherein the desired average diameter is within the range of 1 to 15 µm, and wherein at least 80% of the microparticles in the collection of microparticles have a diameter of 20 µm or less.

In an alternative aspect, the present invention provides a method of making a composition, e.g. a pharmaceutical composition, which method comprises, having produced microparticles, e.g. CMP, according to the method as described above, the step of formulating the microparticles with one or more of a pharmaceutically acceptable excipient, a carrier, a propellant, a buffer, a stabiliser, an isotonicizing agent, a preservative, an antioxidant, or other materials well known to those skilled in the art. Such materials should be non-toxic and should not interfere with the efficacy of the active ingredient.

In an alternative aspect, the present invention provides a method of making a composition, e.g. a pharmaceutical composition, which method comprises, having produced microparticles, e.g. CMP, according to the method as described above, the step of formulating the microparticles with an allergen.

In a further aspect, the present invention provides a method of making a kit, which method comprises, having produced microparticles, e.g. CMP, according to the method as described above, the step of placing an allergen and the microparticles in the kit.

In an alternative aspect, the present invention provides a method of making a composition, e.g. a pharmaceutical composition, which method comprises, having produced microparticles e.g. CMP, according to the method as described above, the step of formulating the microparticles with an antigen.

In a further aspect, the present invention provides a method of making a kit, which method comprises, having produced microparticles, e.g. CMP, according to the method as described above, the step of placing an antigen and the microparticles in the kit.

The (pharmaceutical) compositions and kits, comprising microparticles and an antigen may also comprise a further adjuvant. In U.S. 60/815,074 Applicants have shown that CMP have a synergistic effect when administered with other adjuvants in the same vaccine formulation.

In an alternative aspect, the present invention provides a method of making a delivery device having a reservoir of microparticles, which method comprises, having produced microparticles, e.g. CMP, according to the method as described above, the step of loading the microparticles into the delivery device. The microparticles may be drawn into the nose to the sinuses and upper respiratory tract or through the mouth to the alveolar macrophages by inhalation and/or by a propellant. The delivery device may comprise (a) a reservoir for the microparticles (b) a delivery orifice adapted to locate in a patient's mouth or nose; and (c) a valve between the reservoir and the delivery orifice such that the valve can be operated to control the delivery of the microparticles. A particularly preferred form of device is a nasal spray bottle containing a CMP preparation and optionally a carrier, the spray bottle having a neck adapted for nasal delivery.

In an alternative aspect, the present invention provides the use of a collection of chitin microparticles for the preparation of a medicament for use in a method of treatment selected from the group consisting of treatment of an allergy, treatment of a condition benefiting from up-regulation of the cell-mediated immune system, and treatment of a condition by up-regulating of the activity of NK cells and/or secretion of IFN-γ by cells of the immune system. Preferably the collection of microparticles and/or the particle size distribution of the microparticles in the collection is as described above. For example, the diameters of at least 80% of the chitin microparticles may be within the range of 5 to 20 µm. Preferably the collection of chitin microparticles is produced by the method as defined above.

As discussed above, although therapeutic uses of CMP have previously been disclosed, known methods of producing CMP, such as sonication, are not amenable for industrial scale-up. One method of producing CMP that Applicants considered might be suitable for industrial scale-up was dry powder ball milling. Applicants found this method to be more effective at producing CMP than air-jet milling, which is the method of choice in the pharmaceutical industry for producing uniform powders of drugs for formulation into tablets.

Applicants also compared the therapeutic efficacy of CMP produced by dry powder ball milling with CMP produced using a microfluidising instrument. However, Applicants found that the CMP produced using a microfluidising instrument was more effective than CMP produced by dry powder ball milling in treating asthma in mice. In particular, Applicants found that the CMP produced using a microfluidising instrument resulted in greater reduction in alveolar eosinophils, indicating that treatment reduced the level of asthma, and in a greater reduction of cellular inflammation in the lungs. In addition, Applicants have also shown that CMP produced using a microfluidising instrument provides protection against viral infection.

These results indicate that CMP produced in accordance with the present invention is therapeutically efficacious and has greater efficacy than CMP produced by other methods of producing CMP that may be suitable for industrial scale-up. Thus, the method of the present invention is capable of producing a collection of CMP having a therapeutically efficacious particle size distribution.

In a further aspect, the present invention provides the use of a composition comprising a collection of chitin microparticles and an infectious agent for the preparation of a medicament for the prophylaxis or treatment of a condition mediated by the infectious agent. Preferably the collection of microparticles and/or the particle size distribution of the microparticles in the collection is as described above. For example, the diameters of at least 80% of the chitin microparticles may be within the range of 5 to 20 µm. Preferably the collection of chitin microparticles is produced by the method as defined above.

In an alternative aspect, the present invention provides a collection of chitin microparticles. Preferably the collection is formulated as a composition such as a pharmaceutical composition, e.g. comprising a therapeutically effective amount of chitin microparticles. Preferably the collection of microparticles and/or the particle size distribution of the microparticles in the collection is as described above. For example, the diameters of at least 80% of the chitin microparticles may be within the range of 5 to 20 µm. Preferably the collection of chitin microparticles is produced by the method as defined above.

In an alternative aspect, the present invention provides a delivery device for the administration of a collection of chitin microparticles comprising:
 (a) a reservoir for the microparticles;
 (b) a delivery orifice adapted to locate in a patient's mouth or nose; and
 (c) a valve between the reservoir and the delivery orifice such that the valve can be operated to control the delivery of the microparticles. Preferably the collection of microparticles and/or the particle size distribution of the microparticles in the collection is as described above. For example, the diameters of at least 80% of the chitin microparticles may be within the range of 5 to 20 µm. Preferably the collection of chitin microparticles is produced by the method as defined above.

In an alternative aspect, the present invention provides a kit comprising:
 (a) a collection of chitin microparticles as defined above;
 (b) an allergen or an antigen from an infectious agent;
 for simultaneous or sequential administration to a patient. Preferably the collection of microparticles and/or the particle size distribution of the microparticles in the collection is as described above.

For example, the diameters of at least 80% of the chitin microparticles may be within the range of 5 to 20 µm. Preferably the collection of chitin microparticles is produced by the method as defined above.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description. Embodiments of the present invention are further described by way of example and not limitation with reference to the accompanying figures.

BRIEF DESCRIPTION OF THE DRAWINGS

The following detailed description, given by way of example, but not intended to limit the invention solely to the specific embodiments described, may best be understood in conjunction with the accompanying drawings, in which.

DETAILED DESCRIPTION

Figure 1:
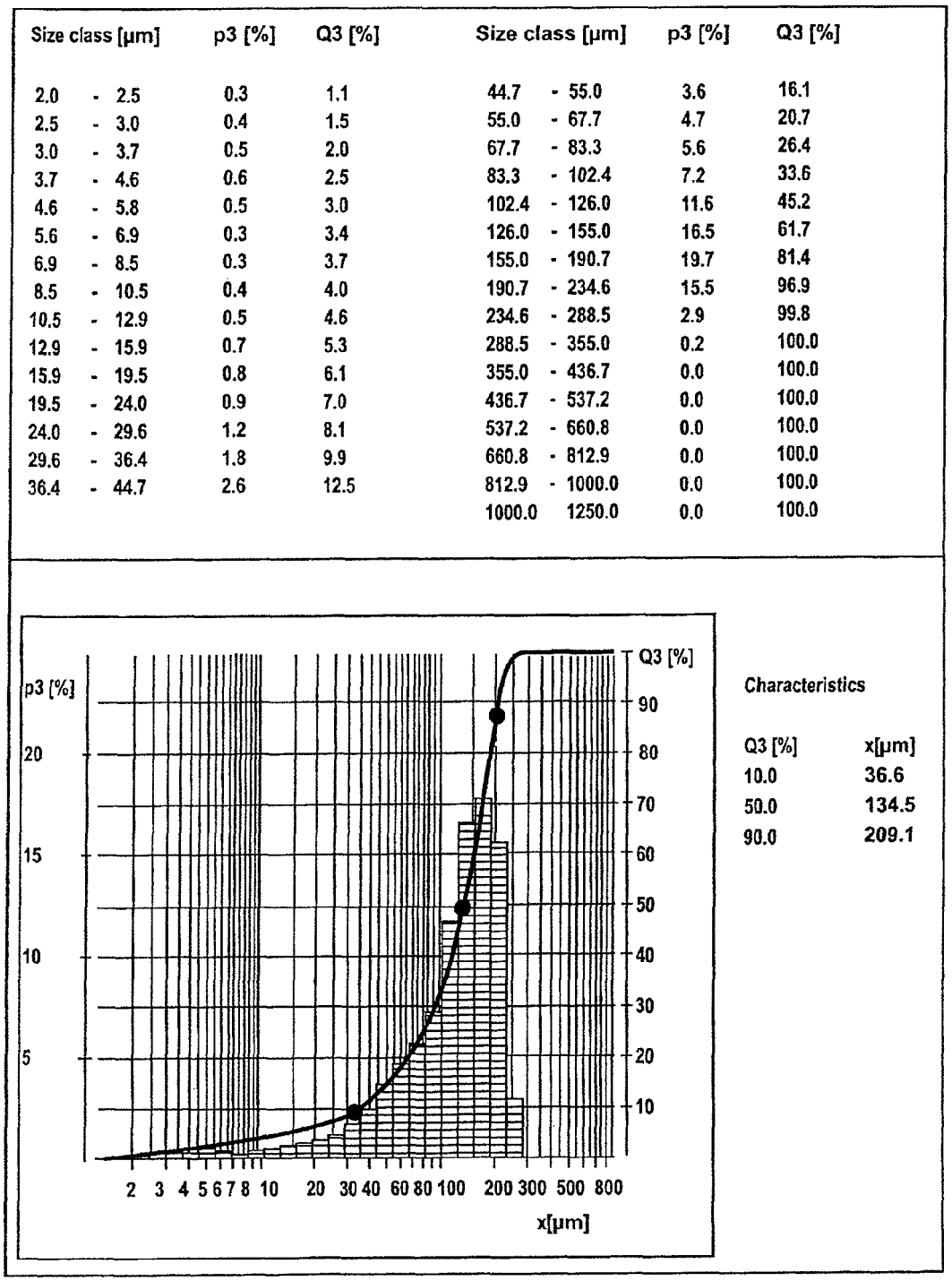
FIG. 1 shows the typical particle size distribution of chitin powder produced by a chitin manufacturer (i.e. the raw material for the production of CMP).

Pharmaceutical compositions and therapeutic uses of CMP are described in Applicants' earlier applications WO 03/015744 and U.S. 60/815,074, which are incorporated herein by reference.

Pharmaceutical compositions and medicaments comprising microparticles, such as CMP, may be used in a method of treating a patent suffering from allergy. Examples of allergies that are amenable to treatment with the pharmaceutical compositions include seasonal respiratory allergies, commonly referred to as hay fever; allergy to aeroallergens including house mite dust, fungal spores, grass pollens, tree pollens and animal danders; allergy treatable by reducing serum IgE and eosinophilia; asthma; eczema and food allergies; dermatitis such as atopic dermatitis.

One further specific embodiment involving the treatment of allergy is in the treatment of horses, and particularly thoroughbred horses, which have a tendency to suffer from allergic conditions such as asthma or recurrent lung infections.

Pharmaceutical compositions and medicaments comprising microparticles, such as CMP, may also be used in a method of treating a patient suffering from a condition that would benefit from the up-regulation of the cell-mediated immune system. Thus the microparticles may be used to strengthen the immune system of an individual. Conditions that benefit from the up-regulation of the cell-mediated immune system include the treatment of microbial infections, including bacterial infections, fungal infections and viral infections, particularly among vulnerable patient groups such as the elderly, premature babies, infants, transplantation patients, immunosuppressed patients such as chemotherapy patients, hospital patients at risk of opportunistic infection, patients on ventilators, cystic fibrosis patients and patients with AIDS. The microparticles and pharmaceutical compositions comprising microparticles are particularly applicable to the treatment of ear, nose, throat and lung infections.

Specific examples of bacterial infection include infection by microorganisms such as *Pseudomonas aeruginosa, Streptococcus* species such as *Streptococcus pneumoniae, Streptococcus pyrogenes, Streptococcus agalactiae, Haemophilus influenza, Klebsiella pneumoniae, Yersinia enteocolitica, Salmonella, Listeria*, Mycobacterial infections including *Mycobacterium tuberculosis, Mycobacterium leprae*, parasitic infections including *Leishmania species* and *Schistosoma* species.

One condition caused by microbial infection, typically by *Streptococcus pneumoniae*, is recurrent ear infections such as Otitis media. These conditions occur in children and adults and are currently treated using antibiotics. It would be advantageous to use the chitin microparticle compositions and medicaments of the invention to treat these conditions and reduce the need for antibiotics.

The preparations of the invention can be used in the treatment of tuberculosis either to treat an existing infection or to protect vulnerable patient groups from infection. Other examples of microbial infections include bacterial pneumonias, such as ventilator-associated pneumonia, and cystic fibrosis associated infections.

Examples of fungal infections include fungal infections such as invasive pulmonary aspergillosis and invasive pulmonary candidiasis, *Pneumocystis carinii* pneumonia, *Coccidioides* and *Crytococcus* infections, e.g. in immunosuppressed patients.

Examples of viral conditions include pulmonary viral infections such as respiratory syncytial virus bronchiolitis, especially in infants and the elderly, or influenza virus, including H5N1, or rhino virus. Numerous studies have shown that during the progression of AIDS, mononuclear cells lose their ability to secrete IL-2, IL-12 and IFN-γ and produce increased levels of IL-4, which allows the HIV virus to proliferate. Therefore treatment with the pharmaceutical compositions of the invention will be useful in reducing the progression of HIV infection by restoring IL-12 and IFN-γ levels.

Pharmaceutical composition and medicaments comprising microparticles, such as CMP, may also be used in the treatment of conditions treatable by up-regulation of the activity of NK cells and/or secretion of IFN-γ by cells of the immune system. An example of such a condition is cancer, and especially lung cancer, lung carcinoma or nasal-pharyngeal carcinoma.

Pharmaceutical compositions comprising microparticles, such as CMP, and an allergen, or kits comprising microparticles, such as CMP, and an allergen, can be employed in the treatment of allergies and allergic symptoms, such as anaphylactic shock, which are associated with conventional desensitisation therapy. Allergens can be readily extracted from food and are commercially available as they are used in the diagnosis and treatment of allergy. In particular, the pharmaceutical composition and kits may be used in the treatment of food allergy. Examples of common food allergens include milk, wheat, gluten, eggs, nuts or shellfish. Such pharmaceutical composition and kits may be also be used in the treatment of horses.

Pharmaceutical compositions comprising microparticles, such as CMP, and an antigen, or kits comprising microparticles, such as CMP, and an antigen may be employed for use in the prophylaxis and treatment of infections and associated symptoms, and conditions caused by an infectious agent. The antigen may be an antigen from an infectious agent. The antigen may be natural, synthetic or derived by recombinant DNA technology. The pharmaceutical compositions may be vaccine compositions. They may therefore contain an antigen, consisting of whole organisms, either killed or weakened, or parts of such organisms, which are used to confer immunity against the condition that the organism causes. By way of example, the infectious agent may cause and/or mediate a bacterial infection, a fungal infection, a viral infection or a parasitic infection.

Thus, in a further aspect, the present invention provides a method for vaccinating a patient against a condition medicated by an infectious agent, the method comprising administering to a patient in need thereof a composition comprising CMP, as defined herein, and an antigen, wherein the CMP and antigen are present in the composition in a therapeutically or prophylactically effective amount.

In U.S. 60/815,074 Applicants found that an administration pattern in which compositions comprising CMP and an antigen were administered at least two times per week, and more preferably at least three times per week, enhanced the protective response raised against the infectious agent when compared to a more usual pattern of administration in which an initial immunisation is followed by a secondary booster after a gap of several weeks.

The pharmaceutical compositions comprising microparticles, such as CMP, and an antigen, or kits comprising microparticles, such as CMP, and an antigen may be employed for the treatment or prevention of malaria, influenza or HIV. Examples of antigens that can be employed in accordance with the present invention include influenza hemagglutinin (HA) vaccines prepared from inactivated virus such as H5N1, H1N1, H3N2, HIV vaccines containing HIV-DNA or HIV antigens, anthrax vaccines such as those containing recombinant Protective Antigen (PA), haemophilus influenza antigens and human papilloma virus antigens such as E7 protein. In common with many infectious agents, antigens suitable for inclusion in pharmaceutical compositions for vaccinating against malaria are known in the art.

The pharmaceutical compositions and kits, comprising microparticles, such as CMP, and an antigen may also comprise a further adjuvant. Examples of other adjuvants that might be employed in the pharmaceuticals compositions and kits include adjuvants based on cholera toxins such as cholera holotoxin (CT) or cholera toxin B subunit (CTB), synthetic CpG DNA and adjuvants based on bacterial cell wall products. The use of adjuvants is reviewed F. Vogel, M. Powell and C. Irving, "A Compendium of Vaccine Adjuvants and Excipients (2nd Edition)", available on the NIH website at: http://www.niaid.nih.gov/daids/vaccine/pdf/compendium.pdf Cholera toxin subunit B (CTB) is a potent mucosal adjuvant, although it can produce unwanted side effects. These can be reduced by adding small amounts (0.1-2%) of the cholera holotoxin. CTB stimulates the local mucosal cellular immune response as well as the systemic IgG response and is commonly used in experimental nasal vaccines (Vadolas et al. 1995. European journal of Immunology 25, 969).

Bacteria-derived adjuvants include peptidoglycan or lipopolysaccharide derivatives such as muramyl-L-alanyl-D-isoglutamine (MDP), monophosphoryl lipid A (MPL), trehalose dimycolate (TDM), cholera toxin B subunit (CTB), CpG DNA, immunostimulatory cytokines including IL-12 and IFN and GM-CSF.

A range of delivery routes may be used for delivering the microparticles, e.g. CMP, and pharmaceutical compositions and medicaments comprising microparticles, such as CMP, to individuals in need thereof. Preferably, these include delivery by the sub-lingual or oral routes, delivery by injection, for example by subcutaneous injection and intramuscular injection, as well as delivering the microparticles intranasally (e.g. to the sinuses and upper respiratory tract using an intranasal spray), or by inhalation, e.g. targeting alveolar macrophages in the lungs. The microparticles, pharmaceutical compositions and medicaments may be administered to a patient via a mucosal or a non-mucosal delivery route. Mucosal delivery route includes intranasal delivery, sublingual delivery, oral delivery, delivery in eye drops and delivery by inhalation. Mucosal delivery routes may comprise sublingual delivery to, for example, buccal mucosa; oral delivery to, for example, gut mucosa; delivery in eye drops to, for example, eye mucosa; intranasal delivery to, for example nose mucosa and mucosa of the upper respiratory tract; and delivery by inhalation to, for example, mucosa of the upper and lower respiratory tract such as lung mucosa. In some aspects of the present invention mucosal delivery routes are preferred as they may provide one or more of the following advantages compared to non-mucosal routes, namely safety, ease of administration as they do generally require a clinician to administer the vaccination as is usually the case for injection, ease of distribution, reduced production cost and improved immunological response as mucosal delivery may activate both the cellular and humoral immune responses.

Non-mucosal delivery route comprises delivery by injection, for example, delivery by subcutaneous injection or intramuscular injection.

Preferably, the microparticles, e.g. CMP, and pharmaceutical compositions and medicaments comprising microparticles, such as CMP, are given to an individual in a "prophylactically effective amount" or a "therapeutically effective amount" (as the case may be, although prophylaxis may be considered therapy), this being sufficient to show benefit to the individual, e.g. providing alleviation of allergy or another condition or prophylaxis for an acceptable period. Typically, this will be to cause a therapeutically useful activity providing benefit to the individual. The actual amount of the compounds administered, and rate and time-course of administration, will depend on the nature and severity of the condition being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980 and Remington's Pharmaceutical Sciences, 19th edition, Mack Publishing Company, 1995. The compositions are preferably administered in dosages of between about 0.01 and 100 mg of active compound per kg of body weight, and more preferably between about 0.5 and 10 mg/kg of body weight. By way of example, this could be achieved using a nasal delivery bottle to deliver 4-8 doses of approximately 0.25 ml of a 5 mg/ml solution of microparticles.

Preferably, the medicaments and compositions set out above are for administration to humans. Preferred patient groups for intranasal treatment with CMP would include those suffering from seasonal allergic rhinitis and sinusitis, or chronic respiratory allergies such as house dust mite allergy and who are currently taking steroids or antihistamines. Other groups include hospitalised patients being treated for chronic lung disorders including infections and lung carcinomas.

The pharmaceutical compositions and medicaments may also include one or more of a pharmaceutically acceptable excipient, a carrier, a propellant, a buffer, a stabiliser, an isotonicizing agent, a preservative, an antioxidant, or other materials well known to those skilled in the art. Such materials should be non-toxic and should not interfere with the efficacy of the active ingredient.

Preservatives are generally included in pharmaceutical compositions to retard microbial growth, extending the shelf life of the composition and allowing multiple use packaging. Examples of preservatives include phenol, meta-cresol, benzyl alcohol, para-hydroxybenzoic acid and its esters, methyl paraben, propyl paraben, benzalconium chloride and benzethonium chloride. Preservatives are typically employed in the range of about 0.1% to 1.0% (w/v).

The invention will now be further described by way of the following non-limiting examples.

EXAMPLES

1. Evaluation of Methods for the Production of CMP

Various methods of producing particles were evaluated as methods for producing CMP.

Particle size and particle size distribution was determined using an AccuSizer 780 Optical Particle Sizer, which is manufactured by Particle Sizing Systems.

The typical size distribution of standard milled chitin powder obtained from the manufacturer is shown in FIG. 1.

Production of CMP by Dry Ball Milling

Figure 2:
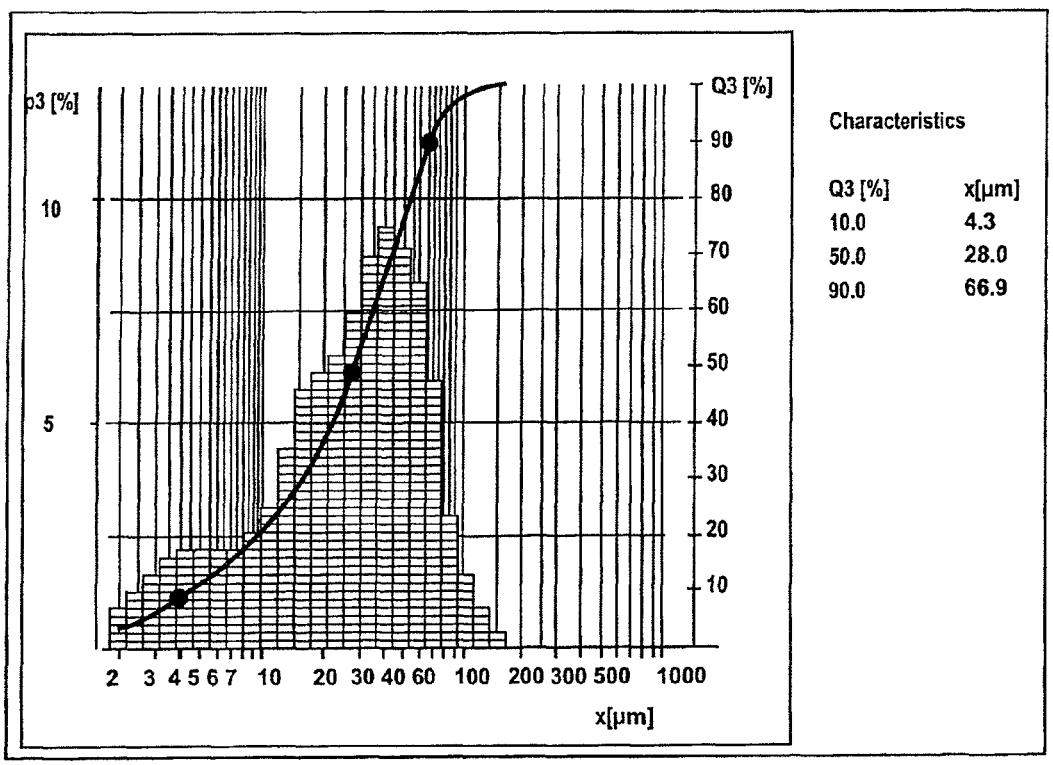
FIG. 2 shows the particle size distribution of chitin particles produced by ball milling chitin powder.

Dry powder ball milling was evaluated as a method for producing CMP. Milling was performed by Heppe GmbH using a bench top ball mill. The final particle size distribution is shown in FIG. 2. However, this method was found to be unsatisfactory for several reasons:

1. The time required for ball milling was excessive and in the order of days of continuous milling. This is not practical for industrial scale-up.
2. The extended milling times is likely to produce heavy metal contamination from ware to the metal balls used in the mill.
3. The ball milling produced an average particle size of around 50 µm instead of the preferred average of around 10 µm.
4. The ball milling produced a heterogeneous population of particles with an excessively large proportion of large particles in the 50 µm+range. These large particles are not desired as they would result in blocking of the nasal delivery device used to apply CMP clinically and are likely to be too large to be phagocytosed and would therefore be unlikely to be pharmaceutically active.

Production of CMP by Air Jet Milling

The standard industrial method for reducing particle size is air jet milling, and this is the method of choice in the pharmaceutical industry for producing uniform powders of drugs for formulation into tablets etc. The method relies on shattering caused by high velocity impact between particles in a high pressure air jet. Air jet milling (air jet micronization) was performed by Micron Technologies Ltd. Air jet micronization is described on the Micron Technologies Ltd. website as "a well proven technique that consistently produces particles in the 1-30 micron range". Table 1 shows the results of air jet milling using 100 g of the chitin powder as shown in FIG. 1.

TABLE 1

| | Average particle diameter |
|---|---|
| Feed | 276.119 µm |
| First pass | 222.093 µm |
| Second pass | 109.386 µm |
| third pass | 116.129 µm |

Evaluation of this method for production of CMP showed that even after the third pass the average particle diameter was still 116.129 µm. This method was therefore considered to be completely ineffective for producing CMP. This is because chitin is composed of laminated fibres similar to wood, which have considerable resilience and elasticity and therefore resist impact shattering. The nature of chitin is fundamentally different from drug formulation particles, which consist of salt crystals with a glass like structure that readily shatters on impact.

Production of CMP Using a Microfluidising Instrument

The microfluidising instrument used in these experiments was the Microjet Laboratory Processor Model 100. This instrument produces pressure by the use of an air motor. Air pressure pushes a large piston, which in turn pushes a smaller piston plunger in an intensifier pump. The plunger transfers pressure to the product stream, which is forced through diamond microchannels. A stainless steel isolator prevents any possibility of product contamination from the air supply or carryover of product into the air motor.

The starting material was chitin powder having a particle size distribution as shown in FIG. 1.

Figure 3:
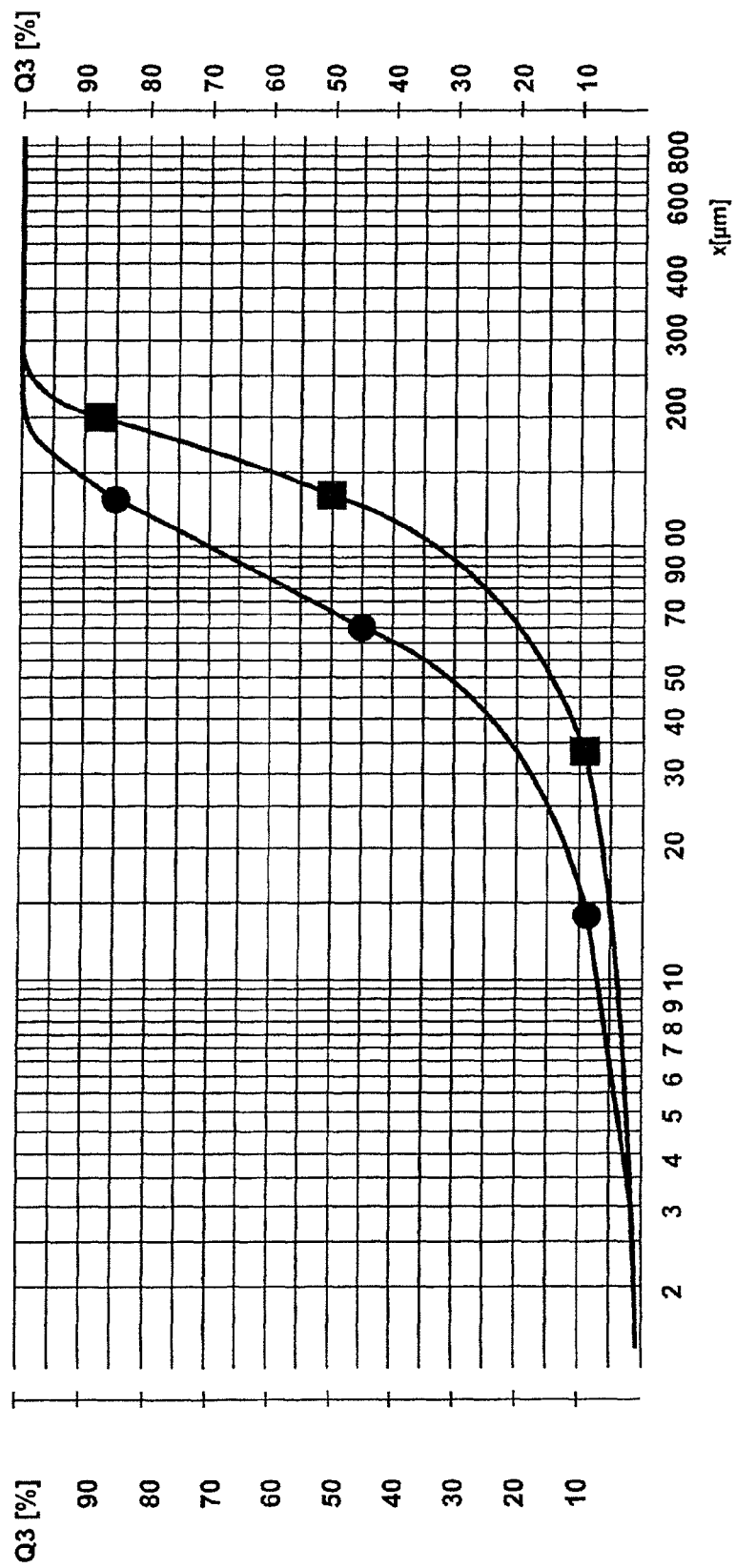
FIG. 3 shows the effect of sieving on the particle size distribution of chitin powder, produced by a chitin manufacturer. The circles indicate sieved chitin powder and the squares indicate unsieved chitin powder.

The chitin powder was first sieved through a 126 µm sieve using the Endecotts Sieve Shaker. FIG. 3 shows the effect of sieving on particle size distribution. Sieving the chitin powder prior to passing it through a microfluidising instrument was found to provide a number of advantages. It was found that the smaller the starting size, the greater the yield of CMP. Sieving the chitin powder also prevents blockage of the microfluidising instrument, thereby allowing milling of the preferred concentration of final product, which is 5 mg/ml.

A few grams of Purified Water were added to approximately 2.00 g of Chitin to form a paste. This was then gradually added to the Product Inlet Reservoir of a Microjet Laboratory Processor Model 100, which contained approximately 500 g of Purified Water. This solution was passed though the fluidiser 3, 6, 9 and 12 times, at each of the time points samples were taken for particle size analysis. The operating pressure of the microfluidising instrument was 20,000 to 23,000 psi.

The experiments showed that 9 passes through the microfluidising instrument produced the optimum CMP product. The optimum characteristics for CMP are: The average diameter of the CMP is around 10 µm+/−5 µm and 80% of the CMP have a diameter of 20 µm or less; 1% or less of the CMP have a diameter of greater than 50 µm.

Table 2 shows the numerical mean, mode and median particle size after 3, 9 and 12 passes through the microfluidising instrument.

TABLE 2

| No. passes | mean (µm) | mode (µm) | median (µm) |
|---|---|---|---|
| 3 | 30.11 | 25.38 | 26.84 |
| 9 | 10.49 | 11.01 | 8.81 |
| 12 | 12.11 | 9.85 | 9.56 |

Figure 4A:
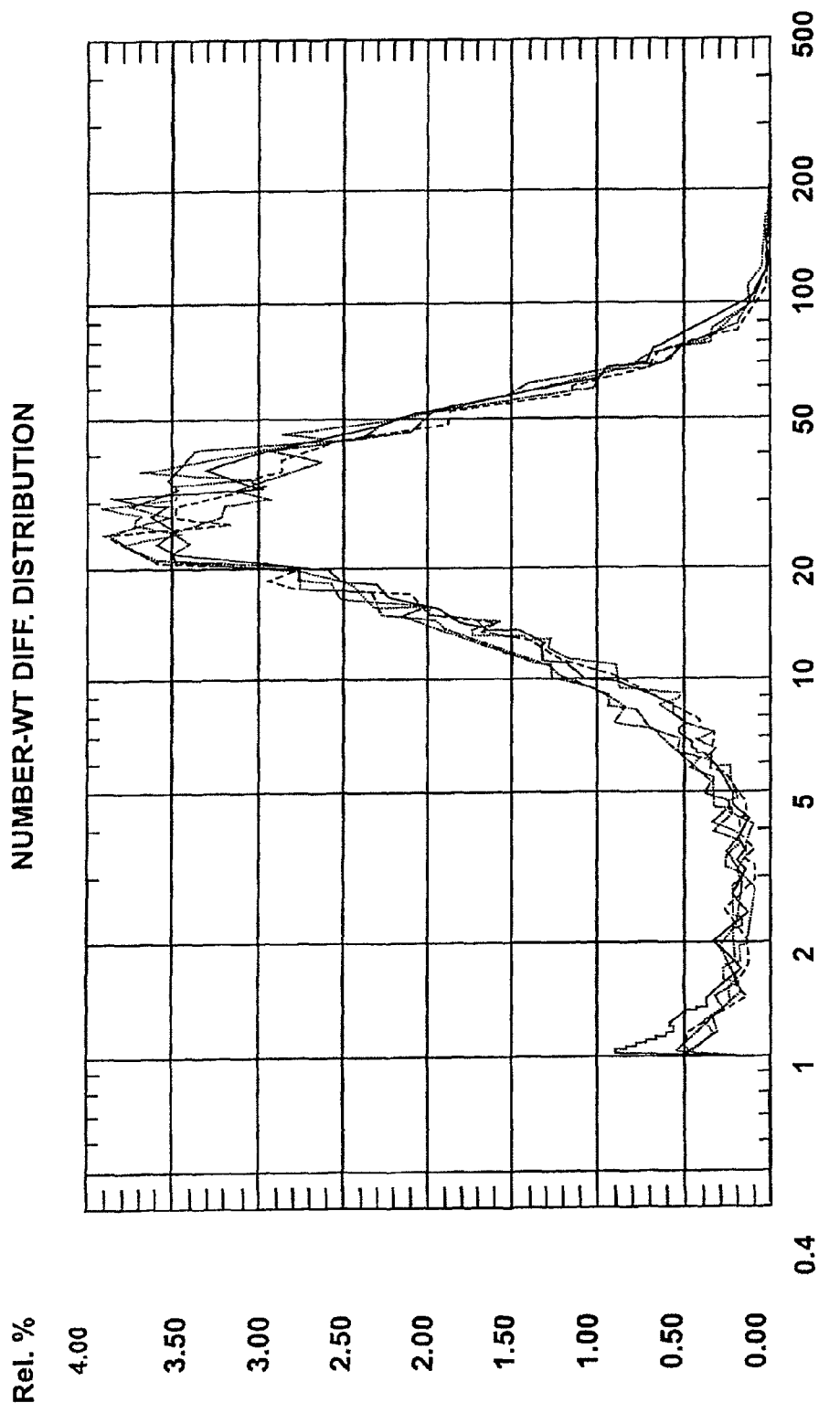
FIG. 4 shows the particle size distribution of CMP after passing a chitin powder suspension through a microfluidising instrument; (a) particle size distribution after three passes; (b) particle size distribution after nine passes; (c) particle size distribution after twelve passes. Measurement of particle size distribution was repeated four times.
Figure 4B:
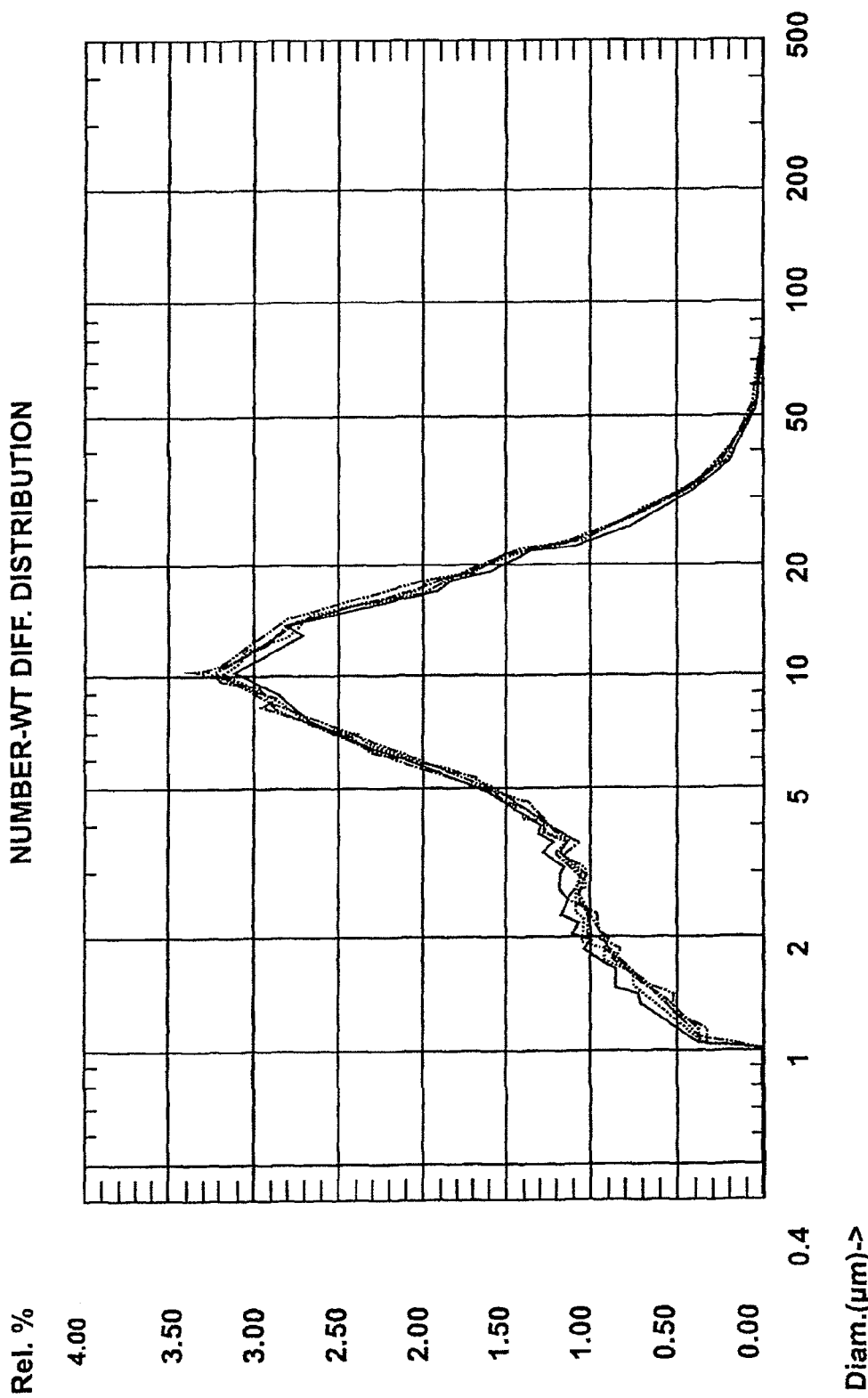
Figure 4C:
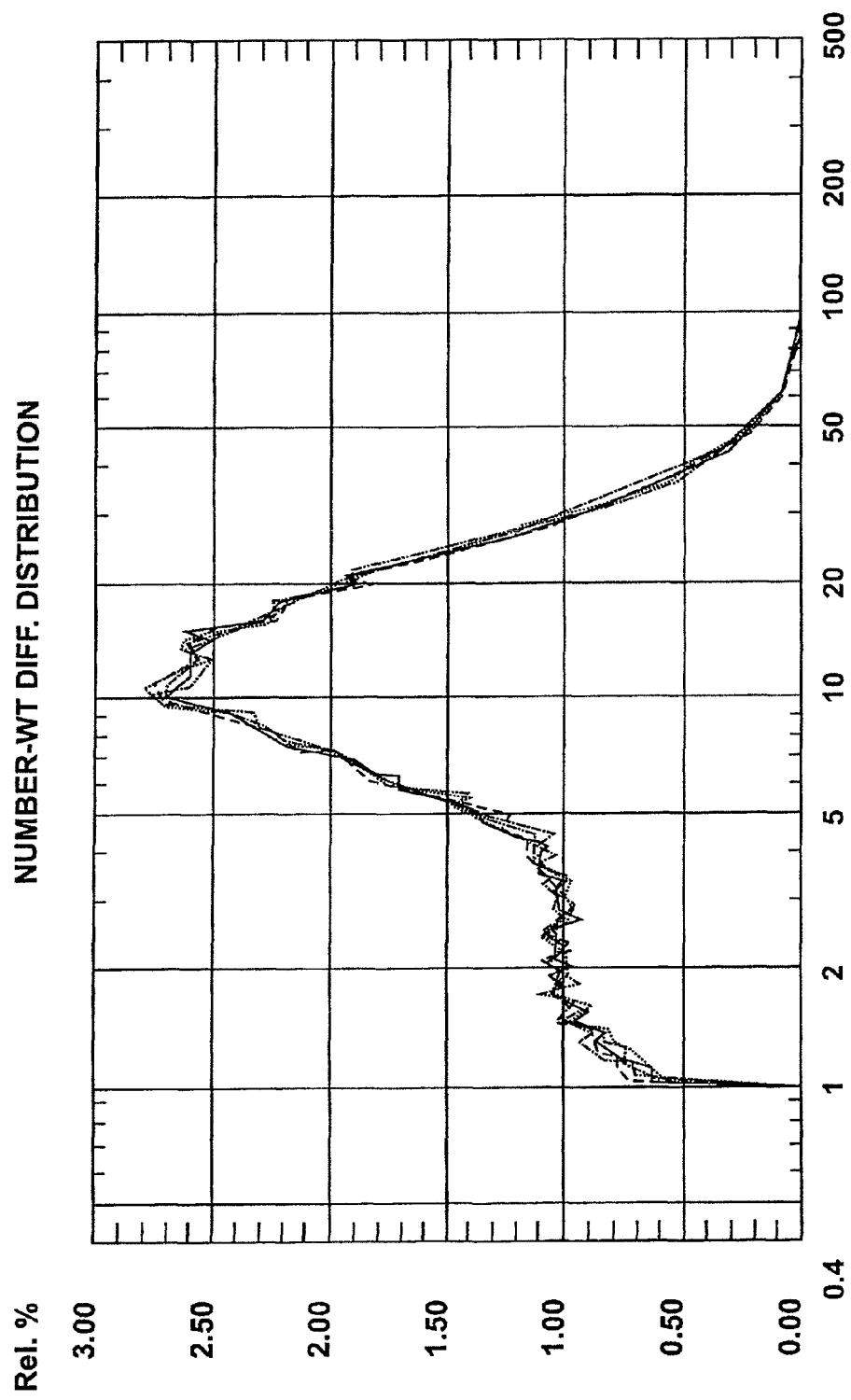
Figure 5:
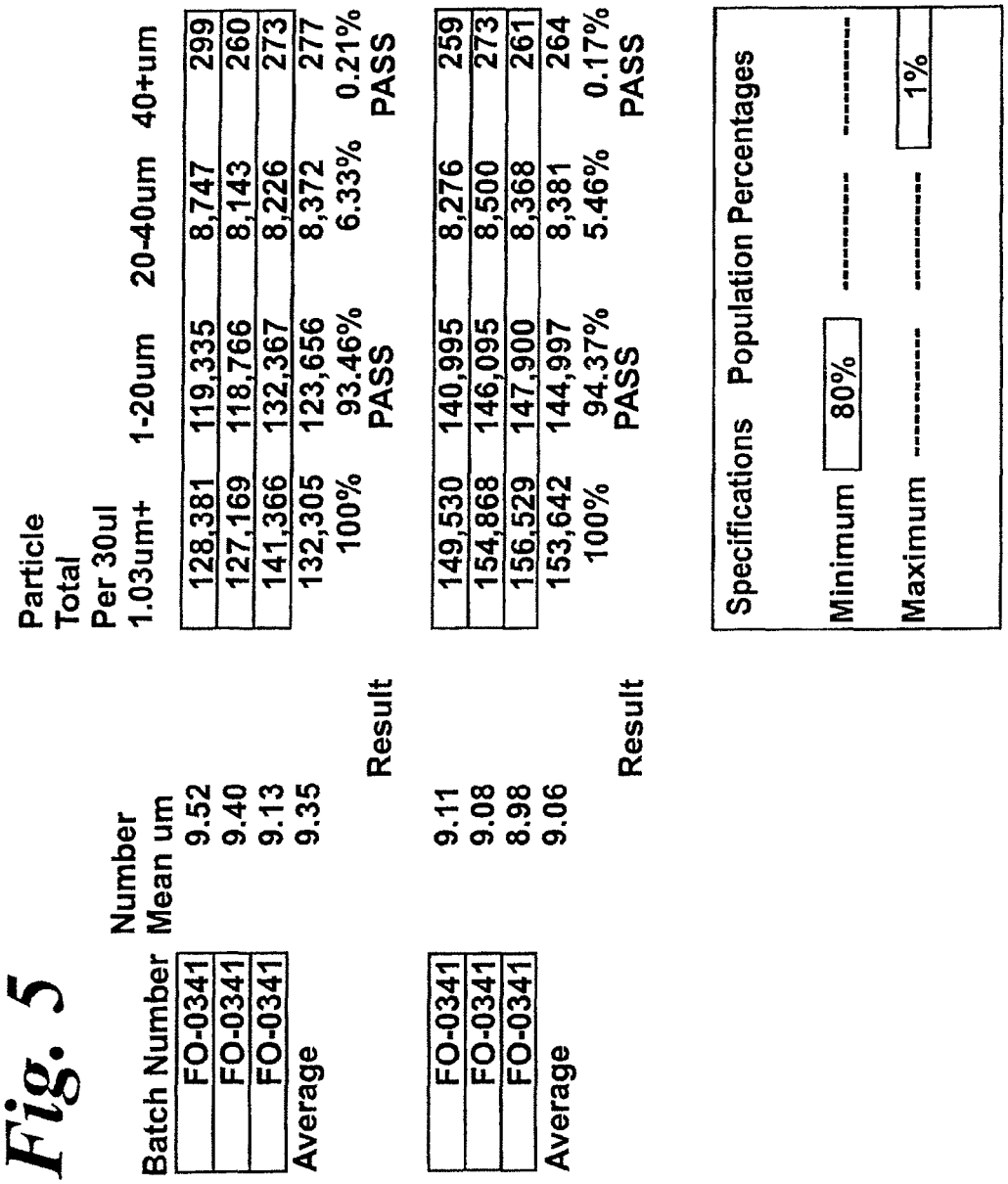
FIG. 5 shows the CMP produced to optimum specifications by pre-sieving the chitin powder and nine passes in the microfluidising instrument.

FIG. 4 shows the particle size distribution after 3, 9, and 12 passes through the microfluidising instrument respectively. Particle size reduced progressively after 3, 6, and 9 passes. 3 passes (FIG. 4a) was not optimum for the production of CMP (average=30.11 µm). The optimum number of passes was determined to be 9 (FIG. 4b), which gave an average particle size of 10.49 µm. An increase to 12 passes (FIG. 4c, average=12.11 µm) did not produce any significant improvement over this. FIG. 5 shows the CMP produced to optimum specifications by pre-sieving the chitin powder and nine passes in the microfluidising instrument.

2. Evaluation of Chitin Microparticles Made by Different Methods in a Mouse Model of Acute Asthma Method Mice were treated intranasally with a series of 100 µg doses of chitin microparticles (CMP) given prophylactically before being made allergic to ovalbumin (OVA) by intraperitoneal injections of OVA. The mice were subsequently given 100 µg intranasal doses of chitin microparticles on the same day as an intratracheal challenge with OVA. The day following the final OVA challenge and treatment mice were sacrificed and lung histopathology examined by microscopic analysis of lung sections. Eosinophil counts were also performed in lung lavage washings. Comparison was made with mice sensitized and challenged in the same way but treated only with PBS (phosphate buffered saline).

The mice were treated with either chitin microparticles made by ball milling as described in Example 1 (CMP000) or chitin microparticles made using a microfluidising instrument as described in Example 1 (CMP001).

Results

CMP001 resulted in greater reduction in eosinophils in the lungs.

Figure 6:
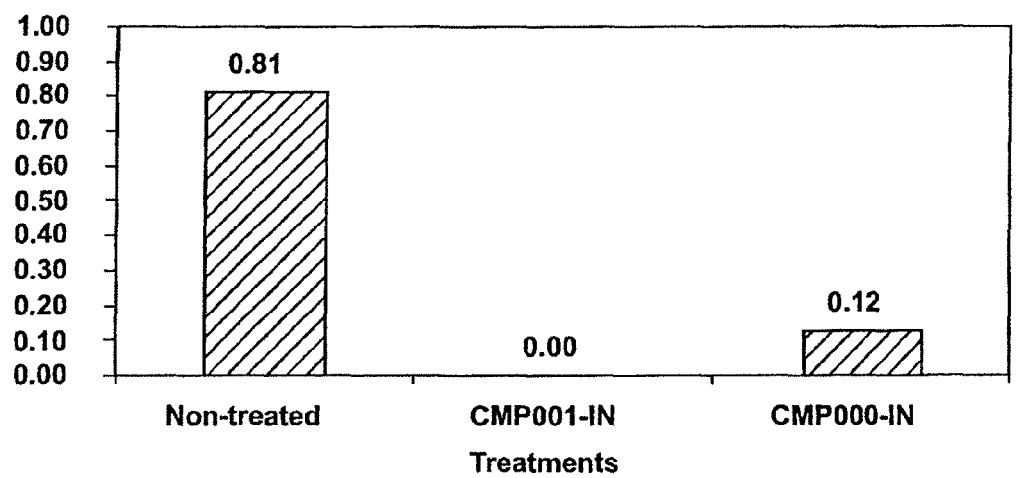
FIG. 6 shows the eosinophil count in bronchopulmonary lavage in mice treated prophylactically with CMP and challenged with ovalbumin. CMP000 refers to CMP produced by ball-milling and CMP001 refers to CMP produced using a microfluidising instrument.

In the asthma model, mice treated with either CMP000 or CMP001 showed a much greater reduction in alveolar eosinophils obtained in the lavage indicating that treatment reduced the level of asthma. However, the CMP made by microfluidization (CMP001) had a greater beneficial effect than CMP produced by ball milling (CMP000) (FIG. 6). Therefore treatment with high-shear microfluidized CMP (CMP001) was superior to CMP produced by ball milling (CMP000) in reducing eosinophil levels in the lungs of asthmatic mice.

CMP001 resulted in greater reduction in histopathology in the lungs.

Figure 7:
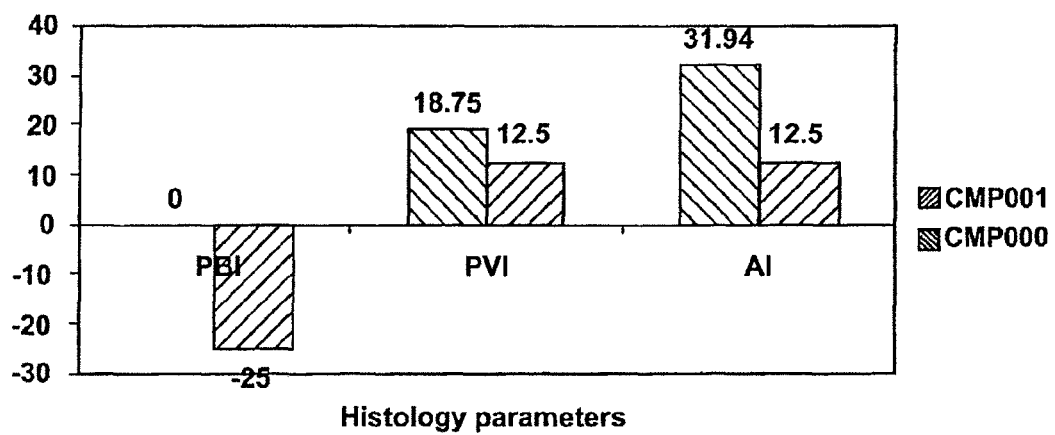
FIG. 7 shows the reduction in lung inflammation in mice treated prophylactically with CMP and challenged with ovalbumin relative to non treated asthma group. PBI=Peribronchial inflammation, PVI=Perivascular inflammation, AI=Alveolar inflammation. CMP000 refers to CMP produced by ball-milling and CMP001 refers to CMP produced using a microfluidising instrument.
Figure 8:
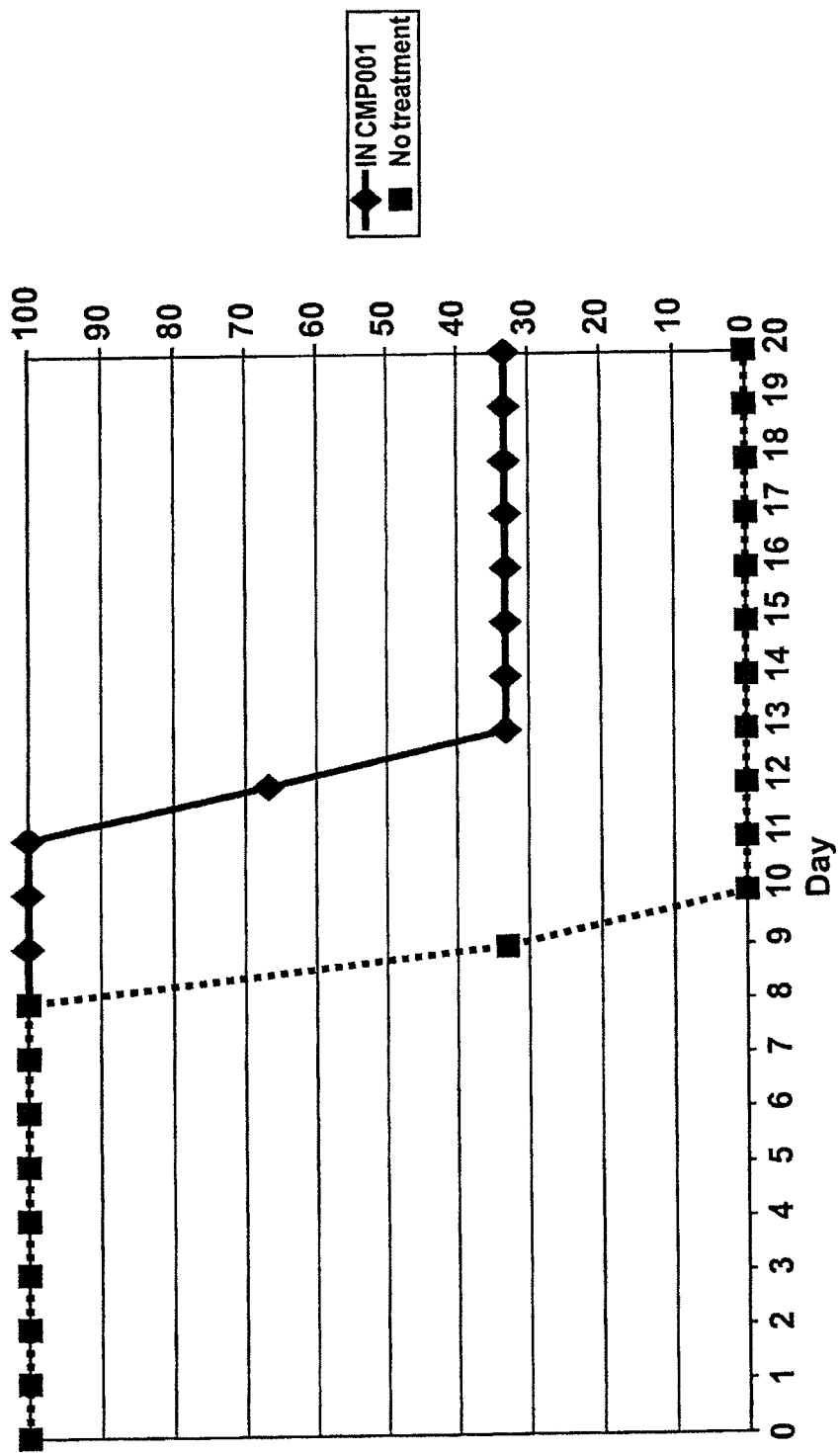
FIG. 8 shows the survival of mice treated prophylactically with CMP (produced using a microfluidising instrument) and infected with the H5N1 virus (day 0). Diamonds indicate treatment with CMP, squares indicate no treatment.

Cellular inflammation is a marker of the asthmatic lung and is measured by counting the number of inflammatory cells that accumulate in the walls of the airways (Peribronchial inflammation) or around the blood capillaries (Perivascular inflammation) or in the alveolar sacs (Alveolar inflammation). The results (FIG. 7) show that CMP001 was superior in all three parameters in reducing the inflammation.

3. CMP Prophylaxis Against H5N1 Viral Infection in a Mouse Challenge Model

Method

Mice were given 100 μg chitin microparticles intranasally at −48 h, −24*h* and 6 hours prior to intranasal infection with 1000 pfu of H5N1 virus. The CMP were made using a microfluidising instrument as described in Example 1 (CMP001). Survival was monitored for 20 days.

Results

The prophylactic application of intranasal CMP001 increased the number of survivors (FIG. 8). This is believed to be due to the increase in innate immune protection such as increase in NK cell activity and increase in Th1 cytokines such as IFNg produced by the action of CMP on the macrophages and other immune cells in the respiratory mucosa.

References

All publications, patent and patent applications cited herein or filed with this application, including references filed as part of an Information Disclosure Statement are incorporated by reference in their entirety.

1. Shibata et al, J. Immunol., 164: 1314-1321, 2000.
2. Shibata et al, J. Immunol., 161: 4283-8, 1998.
3. Shibata et al, Infection and Immunity, 65(5): 1734-1741, 1997.

4. Shibata et al, J. Immunol., 159: 2462-2467, 1997.
5. Strong, P., H. Clark, and K. Reid, Clin Exp Allergy 32:1794, 2002.
WO 03/015744
U.S. 60/815,074
U.S. Pat. No. 5,690,954
F. Vogel, M. Powell and C. Irving, "A Compendium of Vaccine Adjuvants and Excipients (2nd Edition)".
Vadolas et al. 1995. European journal of Immunology 25, 969.
Remington's Pharmaceutical Sciences, 16th edition, Osol, A. (ed), 1980.
Remington's Pharmaceutical Sciences, 19th edition, Mack Publishing Company, 1995.

* * *

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of producing a chitin microparticle composition which comprises chitin microparticles having an average diameter between 1 and 20 μm, wherein the method comprises:
   (a) making an aqueous suspension of chitin microparticles; and
   (b) passing the aqueous suspension through a microfluidising instrument to reduce the average diameter of the chitin microparticles to the average diameter by forcing the aqueous suspension of chitin microparticles through microchannels at an operating pressure of at least 15,000 psi; wherein the diameter of at least 90% of the microparticles in the chitin microparticle composition is within the range of 1 to 20 μm.

2. The method according to claim 1, wherein the desired average diameter is within the range of 1 to 10 μm.

3. The method according to claim 1, wherein the desired average diameter is a phagocytosable size.

4. A method of producing a chitin microparticle composition which comprises chitin microparticles having an average diameter between 1 and 20 μm, wherein the method comprises:
   (a) making an aqueous suspension of chitin microparticles; and
   (b) passing the aqueous suspension through a microfluidising instrument to reduce the average diameter of the chitin microparticles to the average diameter by forcing the aqueous suspension of chitin microparticles through microchannels at an operating pressure of at least 10,000 psi; wherein the diameter of at least 90% of the microparticles in the chitin microparticle composition is within the range of 1 to 20 μm.

5. A method according to claim 1, wherein the method comprises passing the suspension through the microfluidising instrument at least 7 times.

6. The method according to claim 1, wherein the method comprises sieving the particles prior to passing the suspension through the microfluidising instrument.

7. The method according to claim 1, wherein the method comprises the step of formulating the chitin microparticles with an allergen or an antigen.

8. The method according to claim 7, wherein the method comprises formulating the microparticles with one or more of a pharmaceutically acceptable excipient, a carrier, a propellant, a buffer, a stabiliser, an isotonicizing agent, a preservative or an antioxidant.

9. The method according to claim 7, wherein the allergen is a food allergen.

10. The method according to claim 9, wherein the food allergen is found in milk, wheat, gluten or eggs.

* * * * *